United States Patent [19]

Miller, Jr. et al.

[11] 4,405,657

[45] Sep. 20, 1983

[54] NON-SKID PLASTIC FLOORING PRODUCT AND METHOD OF MANUFACTURE

[75] Inventors: Jesse D. Miller, Jr.; James R. Petzold, both of Lancaster, Pa.

[73] Assignee: Armstrong World Industries, Inc., Lancaster, Pa.

[21] Appl. No.: 353,195

[22] Filed: Mar. 1, 1982

Related U.S. Application Data

[62] Division of Ser. No. 237,666, Feb. 24, 1981, Pat. No. 4,348,447.

[51] Int. Cl.³ .......................... B32B 5/16; B32B 5/26
[52] U.S. Cl. .................................. 427/54.1; 427/197; 427/199; 427/203; 427/204; 427/270; 427/407.1; 428/149
[58] Field of Search .................. 427/54.1, 202, 197, 427/199, 203, 204, 270, 407.1; 428/141, 142, 143, 149, 156, 161, 172, 323, 325, 423.1, 430, 431, 480

[56] References Cited

U.S. PATENT DOCUMENTS

| | | | |
|---|---|---|---|
| 3,267,187 | 8/1966 | Slosberg et al. | 428/143 |
| 3,928,706 | 12/1975 | Gibbons | 428/323 |
| 4,196,243 | 4/1980 | Sachs et al. | 428/147 |

*Primary Examiner*—Paul J. Thibodeau

[57] ABSTRACT

A non-skid decorative plastic floor covering comprised of a decorative plastic base having a plurality of slip-resistant elements positioned on the base with a clear or translucent wear layer overlying the slip-resistant elements and the exposed intervening base. The slip-resistant elements comprise particles, preferably inorganic and rounded, embedded in a cured plastic matrix, the particles being distributed throughout the matrix in a substantially abutting relationship with the upper-most layer of particles protruding from the matrix such that the protruding particles impart a rough, irregular non-skid surface texture to the wear layer overlying the slip-resistant elements.

3 Claims, 3 Drawing Figures

NON-SKID PLASTIC FLOORING PRODUCT AND METHOD OF MANUFACTURE

CROSS-REFERENCE TO RELATED APPLICATION

This is a division of application Ser. No. 237,666, filed Feb. 24, 1981 and now U.S. Pat. No. 4,348,447.

BACKGROUND OF THE INVENTION

1. Field of the Invention

This invention relates to non-skid plastic flooring products and their method of manufacture.

2. Description of the Prior Art

It is known in the prior art to provide, where desirable, non-skid or slip-resistant wear layers. Thus commercial tile having a non-skid surface is conventionally made by heating individual pieces of ordinary vinyl tile, sprinkling the surface with a carborundum grit, and then embedding the grit into the surface of the tile, the grit particles imparting the non-skid characteristic to such tile. It is also known from the prior art to provide a slip-resistant surface by providing the plastic flooring product with a nubbly texture by incorporating particulate plastic material dispersed in the wear coating which is cured to form a textured wear layer. The latter is disclosed in U.S. Pat. No. 4,196,243.

SUMMARY OF THE INVENTION

A non-skid decorative plastic floor covering is provided by positioning a plurality of slip-resistant elements on a decorative plastic base and providing a clear or translucent wear layer overlying the slip-resistant elements and the exposed intervening base. The slip-resistant elements comprise particles, preferably inorganic and rounded, embedded in a cured plastic matrix, the particles being distributed throughout the matrix in a substantially abutting relationship with the upper most layer of particles protruding from the matrix such that these protruding particles impart a rough, irregular, non-skid surface texture to the wear layer overlying the slip-resistant elements. The method of manufacture includes the steps of: (a) providing a decorative base layer, (b) applying curable elements in a preselected pattern to the base layer, the curable elements being of sufficient thickness such that when the particles are applied thereto and embedded therein there is curable matrix material in an amount sufficient to bind together the abutting particles after they have been embedded in the matrix in a substantially abutting relationship, but only in an amount sufficient to hold the upper most layer of particles while allowing such particles to protrude from the matrix, (c) applying particles to the matrix elements (d) embedding said particles throughout the matrix in a substantially abutting relationship with the upper most layer of particles protruding from the matrix, (e) curing the matrix, (f) applying an overall clear wear layer to form a continuous wear film over the cured elements having the protruding particles and over the intervening base; the upper most layer of particles protruding from the matrix imparting a rough, irregular, non-skid surface texture to the wear layer overlying the slip-resistant elements, and (g) curing the wear layer.

DESCRIPTION OF THE PREFERRED EMBODIMENTS

Figure 1:
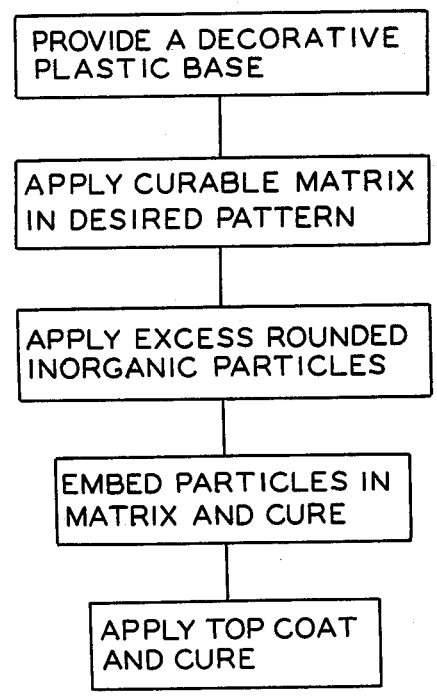
FIG. 1 is a flow diagram setting forth the method by which the non-skid plastic floor covering of this invention is manufactured.

The detailed description which follows is given with reference to the figures of the drawing as applicable.

Decorative Plastic Base

Figure 2:
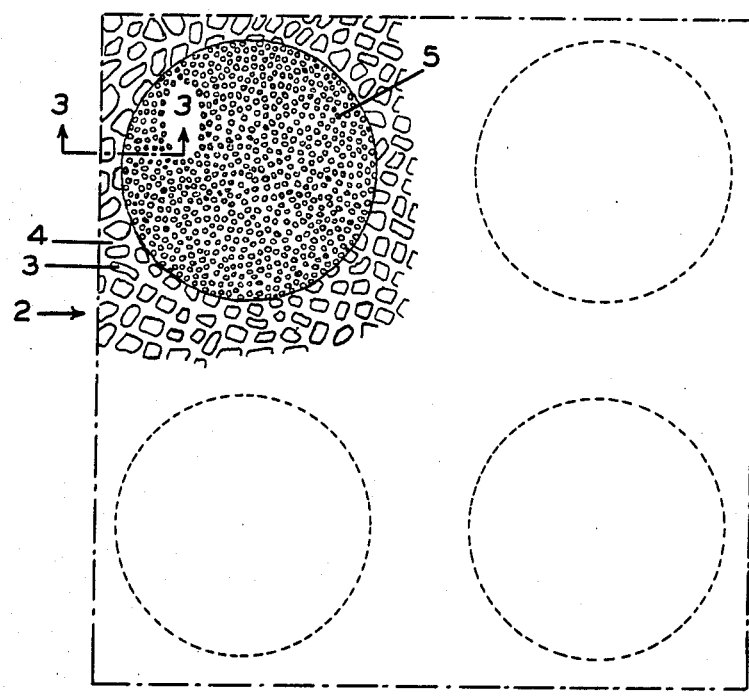
FIG. 2 is a top view of a section of a plastic floor covering produced in accordance with this invention showing the details of one element, indicating positioning of additional elements and showing a section in detail of the surrounding base.

In accordance with our invention any conventional decorative plastic base such as polyvinyl chloride composition tile products, including vinyl-asbestos tile, and plastic sheet products may be used. In the specific embodiment shown in FIGS. 2 and 3 of the drawings, the decorative plastic base is a felt-backed vinyl composition sheet 6' in width. The backing is a conventional cured resin saturated non-woven glass fiber felt. In producing the base an adhesive coat is first applied after which colored fines and chips of plasticized polyvinyl chloride are metered onto the surface and the whole is consolidated under heat and pressure to consolidate the chips and fines and fuse them in a decorative plastic layer firmly adhered to the felt backing. A plastic sheet vinyl base having a design in the configuration indicated by numeral 2 in FIG. 2 is produced, the design comprising small individual chips 3 and mortar lines 4. The thickness of the consolidated vinyl layer is 28 mils (about 7 mm) with the thickness of felt backing being 37 mils (about 8 mm). In addition to substituting tile as a base, either before or after cutting, it will be equally as obvious to one skilled in the art that other plastic base layers either backed with a conventional felt or unbacked and decorated, for example by rotogravure printing, could equally as well be used in the practice of the invention with some slight modifications in the overall process possibly being required depending upon the particular decorative plastic base used.

Curable Matrix

Although it will be readily evident to one skilled in the art that any curable liquid, having the desired viscosity such that it can be applied to the base layer to form the base of the slip-resistance elements, may be used, the practice of the invention as described will be restricted to the use of a heat curable acrylated polyester resin.

Preparation of Acrylated Polyester Curable Matrix

To form the polyester the following ingredients were charged to a 5 liter, 5-necked flask with a glass helicies packed, steam heated partial condenser (upright) with still head and total condenser above. The flask was further equipped with mantle, stirrer, thermometer, temperature controls and gas inlet tube. The ingredients were heated gradually with stirring to 220°±5° C. under nitrogen and held at this temperature until the acid number fell below 1.5±0.5. The nitrogen flow was gradually increased after about 70 percent of the theoretical water was obtained to about 700 ml per minute to help remove the water of esterification and drive the reversible equilibrium reaction to completion.

| Ingredients | Parts by Weight |
| --- | --- |
| 1,6-Hexanediol | 363.52 |
| Neopentyl Glycol | 661.25 |
| Cyclohexanedimethanol | 914.13 |
| Phthalic Anhydride | 563.81 |
| Dibutyltin bis Lauryl Mercaptide Catalyst | 2.48 |
| Isophthalic Acid | 1476.24 |
| Silicone Antifoam (Foamkill 8R) | 0.0566 |
| Toluene | 650.00 |

Acrylation of the polyester is carried out by charging 1.2 equivalents of acrylic acid to an appropriately sized 4-necked flask containing the polyester-solvent mixture. Sulfuric acid (0.24 parts per hundred parts resin) is added and the mixture held at reflux with a Barrett trap used to remove the water and return the solvent.

The batch temperature is held at 95° to 110° C. The reaction was terminated when between 90 and 98 percent of the theoretical water was obtained by cooling to 90° C. and adding 1.3 equivalents of magnesium oxide dispersed in 100 parts by weight isodecyl acrylate with an additional 600 parts by weight of isodecyl acrylate also added. The flask was then evacuated to 40 to 50 mm of mercury to remove solvent. Addition with agitation of 73.14 parts by weight 1,6-hexane-diol diacrylate, 104.5 parts by weight acrylic acid, 100 parts by weight isodecyl acrylate, 104.5 parts by weight benzophenone and 62.7 parts by weight catalyst 2,2-dimethoxy-2-phenylacetophenone (Irgacure 651) completes the curable matrix preparation.

UV Curable Clear Wear Coating

The following reactants were charged into a reaction vessel:

| Ingredients | Parts by Weight |
| --- | --- |
| Polyester polyol* | 36.15 |
| 2 Ethylhexyl acrylate | 13.33 |
| 1,6 Hexanediol diacrylate | 9.07 |

*Reaction product of 34.62 parts by weight adipic acid, 13.12 parts by weight isophthalic acid, 48.76 parts by weight 1,6 hexanediol and 3.48 parts by weight glycerine.

23.10 parts by weight of 4,4'diisocyanato dicyclohexylmethane and 0.08 parts by weight of dibutyltin dilaurate catalyst were then added and the mixture reacted at 45° C. to 50° C. After the reaction has proceeded for approximately 45 minutes, 8.67 parts by weight of 2-hydroxyethylacrylate was added and heating and stirring of the reaction mixture continued for two hours at which point the isocyanate functionality is constant.

To this reaction product is then added 1.81 parts by weight benzophenone, 0.90 parts by weight 2,2-dimethoxy-2-phenylacetophenone, 6.78 parts by weight acrylic acid, 0.02 parts by weight 2,6-ditertiarybutyl paracresol antioxidant and 0.09 parts by weight glycolpolysiloxane (DC-193).

Particles

Although the invention as described will utilize preferred rounded inorganic particles, in its broadest application resin particles-including filled vinyl particles may be used as well as mixtures with inorganic particles. When resin particles, filled or unfilled, are used, they must have a minimum hardness of about 50 as measured on a Shore Durometer Hardness Type D tester. Such particles may be prepared from cured thermoset or filled and fused thermoplastic resins. The size range of such particles preferably fall within the particle size distribution range described below for the rounded inorganic particles.

Inorganic Particles

The inorganic particles useful in the practice of the invention to form the roughly textured surface are preferably substantially insoluble in water and have a Mohs hardness of at least about 4 and preferably at least about 6. They must be of a rounded configuration and preferably have a particle size distribution wherein 100% of the particles are larger than about 150 microns, about 80% are between about 300 and 420 microns and none are larger than about 715 microns.

Particularly well adapted for use in the practice of this invention are silica blasting sands produced by Ottawa Silica Co. These conform generally to the following physical analysis:

| | |
| --- | --- |
| AFS grain fineness | 32.4 |
| Size, average Mesh | 43 |
| Size, Mode/mm | .380 |
| Hardness Mohs | 7.0 |
| Specific Gravity | 2.65 |
| Shape | Rounded |

A typical U.S. sieve analysis of these inorganic silica sand particles is as follows:

| U.S. Sieve No. (Mesh) | Size of Openings | Percent Retained |
| --- | --- | --- |
| 30 | 595 microns | 12.4 |
| 40 | 420 microns | 56.8 |
| 50 | 296 microns | 26.7 |
| 70 | 210 microns | 3.5 |
| 100 | 149 microns | 0.6 |

The sand particles are essentially 100% quartz sand, a crystalline silica, and the percent silica dioxide is about 99.808% with the balance of the chemical composition consisting of minor amounts of mixed oxides including iron oxide ($Fe_2O_3$) 0.016%, alumina oxide ($Al_2O_3$) 0.042%, titanium oxide ($TiO_2$) 0.14%, calcium oxide ($CaO_2$) less than 0.1% and magnesium oxide ($MgO_2$), also less than 0.01%.

Both clear particles as well as a variety of colored particles may be used in the practice of the invention. Colored particles are available in a variety of colors from Burns and Russel of Baltimore and these are clear particles which have their surfaces coated with cured pigmented polyester coatings. Minnesota Mining and Manufacturing also provides a variety of colored quartz particles although the pigmented coating is understood to be of a ceramic nature. The particular pigmented coating composition obviously is not critical to the practice of the invention.

Method of Manufacture

By way of illustration, the best mode of manufacture currently is as follows: The base layer which is comprised of a 37 mil felt backing bonded to 28 mils of a consolidated vinyl composition sheet which has been formed by pressing under both heat and pressure a mixture of fines and fine chips to form a design of the configuration shown in FIG. 2 by the numeral 2 is supplied in the form of a continuous sheet 6' in width (1.829 meters). This sheet is fed, with the plastic layer uppermost, beneath a rotary printer which prints a series of round elements in the configuration and position shown in FIG. 2 across the width of the goods at repeated intervals. Twelve mils (about 0.3 mm) of curable matrix of the acrylated polyester composition above described to which has been added one percent by weight benzoyl peroxide, is deposited by the printer with the viscosity being such that it retains its shape to a substantial degree in subsequent processing.

The printed sheet is then next passed beneath a feeder which feeds a mixture of colored and clear quartz particles onto the sheet, those fed onto the round printed elements being directly adhered whereas the excess falling on the intervening base are removed by reversing the direction of feed, a collecting bin being provided to pick up the excess loose chips.

The printed sheet having the quartz particles adhered to the printed element is next fed between two consolidating rolls, the facing roll being set to embed the particles into the uncured matrix. The sheet material is then fed through a hot air oven wherein the acrylated polyester matrix is cured, although the exposed surface of the matrix remains slightly tacky due to oxygen inhibition. The sheet is then passed beneath brushes which remove any loose quartz particles remaining.

The thus prepared sheet is flooded using a roll coater with the liquid photocurable polyurethane coating above described and the flooded sheet is then passed beneath an air knife which directs a blast of hot air to remove excess coating, leaving a thin continuous film conforming in texture to the underlying protruding particles on the slip resistant elements and approximately 4 mils (about 0.1 mm) of coating in the intervening non-printed area.

The coated sheet is then passed beneath a bank of UV lamps where the wear surface is fully cured. The texture imparted to the slip-resistant printed elements conforms to the configuration of the protruding inorganic silica particles which in turn imparts this texture to the overlying cured urethane wear layer, which is between 1 and 2 mils thick.

In order to more clearly show the non-slip characteristics imparted to the flooring product described, a series of tests were run in accordance with military specification MIL-D-17951C (ships) June 5, 1975, Section 3.7 non-slip properties (coefficient of friction). A brief description of the test is as follows:

A 2"×4" foot, loaded to 33 lbs., is drawn across the material at a speed of 7½ feet per minute. The coefficient of friction is determined by the following equation:

$$\text{Coefficient of Friction} = \frac{\text{Recorded Load in Pounds}}{33 \text{ Pounds}}$$

The MIL-D-17951C requirements for a coefficient of friction meeting this military specification are as follows:

| Condition | Leather Foot | | Rubber Foot | |
|---|---|---|---|---|
| | Static | Sliding | Static | Sliding |
| Dry | .60 | .40 | .60 | .50 |
| Wet | .60 | .40 | .60 | .60 |
| Oily | — | — | .60 | .30 |

The flooring product above described (based on the average of 3 tests for each of the conditions examined) gave the following coefficients of friction:

| Condition | Leather Foot | | Rubber Foot | |
|---|---|---|---|---|
| | Static | Sliding | Static | Sliding |
| Dry | .78 | .67 | 1.04 | 1.01 |
| Wet | .72 | .69 | .88 | .84 |
| Oily | — | — | .60 | .54 |

These results clearly show that the non-slip flooring produced in accordance with the method of this invention clearly meets and surpasses the standards of military specification MIL-D-17951C.

Figure 3:
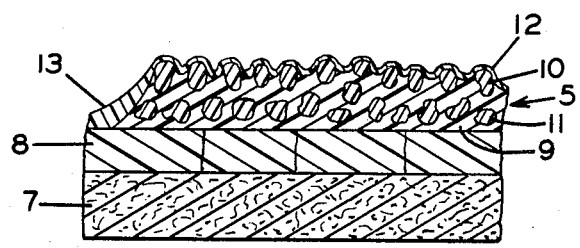
FIG. 3 is an enlarged cross-sectional view taken along the line 3—3 of FIG. 2 showing further details of the product structure.

With reference to FIGS. 2 and 3 of the drawings, details of the finished floor construction are illustrated. As shown in FIG. 2, the top view illustrates the positioning of the slip resistant elements 5 and the design of the plastic base layer comprised of chips 3 and grout lines 4 is illustrated by the numeral 2. An actual 6 cm by 6 cm section is illustrated at about two times enlargement.

FIG 3 is an enlarged cross-sectional view taken along the line 3—3 of FIG. 2. Numeral 7 illustrates the felt backing with the overlying plastic base 8.

In the enlarged cross-section the matrix 9 surrounds the particles 11 embedded therein whereas the uppermost particles 10 protrude from the matrix 9. The clear wear coat 12 conforms to the underlying particles 10. Overlying the base 8 is the thicker clear wear layer 13.

Although the best mode is set forth herein above, it will be obvious to one skilled in the art that one could utilize other curable liquids for forming the matrix and the wear layer. It is preferred that urethane type coatings be used for forming the wear layer since these have proven extremely tough and require minimum care as contrasted with vinyl wear surfaces which require waxing. There is a criticality as to the viscosity for the material which is used to form the matrix into which the inorganic particles are embedded as well as the viscosity of the coating used for the wear layer although the adjustment of such viscosities to meet processing requirements should be readily evident to one skilled in the art. For the matrix usable viscosities would generally fall between 4000 and 12000 centipoises with the 5000 to 6000 range preferred. Sufficient matrix is deposited to hold more than a monolayer of particles but less than an amount that would squeeze over the uppermost layer of protruding particles. The preferred viscosity range for the wear layer coating is from 8000 to 12000 centipoises. Minor variations such as techniques for handling tile versus sheet goods as well as obvious modified techniques for applying the matrix should also be readily evident to one skilled in the art. Coaters other than the roll coater mentioned above could equally as well be used.

Obviously the invention is not to be restricted to the particular designs shown for the non-skid elements and random positioning as well as other configurations for the printed elements such as diamonds, or strips could equally as well be used.

Any departure from the foregoing description which conforms to the invention is intended to be included within the scope of the claims.

What is claimed is:

1. A method of manufacturing a non-skid decorative plastic floor covering comprising:
    (a) providing a plastic base as a liquid matrix;
    (b) applying elements in a preselected pattern to the base, said elements being of a depth and breadth such that when elements are applied to the base and embedded therein, there is curable base material in an amount sufficient to bind together the elements embedded in the base material in substantially abutting relationship but in an amount insufficient to cover the uppermost layer of elements allowing these elements to protrude from the base material;
    (c) said elements are rounded inorganic quartz particles and have a Moh hardness greater than about 4 and a particle size distribution such that none are greater than about 715 microns, about 80% are between about 300 and 595 microns and none are smaller than 150 microns;
    (d) embedding said particles throughout the base material in a substantially abutting relationship with the uppermost layer of particles protruding from the base material;
    (e) curing the base material;
    (f) applying an overall clear or translucent curable wear coating to form a continuous film over the cured base material having the protruding particles in an amount such that a rough skid-resistant texture is imparted to the coating by the underlying protruding particles; and
    (g) curing the wear layer.

2. The method in accordance with claim 1 wherein the curable liquid matrix has a viscosity in the range of about 5000 to 6000 centipoises and wherein the curable liquid coating has a viscosity within the range of about 8000 to 12000 centipoises.

3. The method in accordance with claim 2 wherein the liquid matrix comprises a heat curable acrylated polyester and wherein the wear layer is formed from a coating comprising a urethane having pendent ethylenically unsaturated groups, said coatings being polymerized by exposure to ultraviolet light.

* * * * *